(12) United States Patent
Putman et al.

(10) Patent No.: US 10,179,062 B2
(45) Date of Patent: Jan. 15, 2019

(54) MEDICAL DEVICES AND METHODS FOR PROTECTING A LIMB OF A PATIENT DURING A MEDICAL PROCEDURE

(71) Applicants: J. Michael Putman, Dallas, TX (US); William W. Gardetto, Colleyville, TX (US)

(72) Inventors: J. Michael Putman, Dallas, TX (US); William W. Gardetto, Colleyville, TX (US)

(*) Notice: Subject to any disclaimer, the term of this patent is extended or adjusted under 35 U.S.C. 154(b) by 714 days.

(21) Appl. No.: 14/673,825

(22) Filed: Mar. 30, 2015

(65) Prior Publication Data
US 2016/0287421 A1   Oct. 6, 2016

(51) Int. Cl.
*A61F 5/01*   (2006.01)

(52) U.S. Cl.
CPC .......... *A61F 5/013* (2013.01); *A61F 5/0102* (2013.01)

(58) Field of Classification Search
CPC ........ A61F 5/012; A61F 5/013; A61F 5/0109; A61F 5/0118; A61F 5/0102; A61F 5/0123; A61F 5/0106; A61F 5/0111; A61F 5/0127; A61F 5/0104
USPC ................... 602/13; 128/869, 877–878, 882
See application file for complete search history.

(56) References Cited

U.S. PATENT DOCUMENTS

| | | | | |
|---|---|---|---|---|
| 4,157,713 A | * | 6/1979 | Clarey | A61F 5/05816 128/DIG. 20 |
| 4,168,063 A | * | 9/1979 | Rowland | A63B 71/081 128/DIG. 20 |
| 4,270,527 A | * | 6/1981 | Peters | A61F 5/34 128/DIG. 20 |
| 4,301,791 A | * | 11/1981 | Franco, III | A61F 5/055 128/870 |
| 4,442,834 A | * | 4/1984 | Tucker | A61F 5/05816 128/DIG. 20 |
| 4,470,410 A | | 9/1984 | Elliott | |
| 4,941,458 A | * | 7/1990 | Taheri | A61H 9/0078 601/152 |
| 5,178,162 A | * | 1/1993 | Bose | A61B 46/27 128/849 |
| 5,188,608 A | | 2/1993 | Fritts | |
| 5,190,530 A | | 3/1993 | Greeff et al. | |
| 5,328,445 A | * | 7/1994 | Spahn | A61F 5/05816 128/882 |
| 5,728,053 A | | 3/1998 | Calvert | |

(Continued)

FOREIGN PATENT DOCUMENTS

CN     203355058 U    12/2013

*Primary Examiner* — Kari Rodriquez
*Assistant Examiner* — Camtun Nguyen
(74) *Attorney, Agent, or Firm* — Hubbard Johnston, PLLC

(57) ABSTRACT

Medical devices and methods are presented for protecting a limb, e.g., an arm, of a patient during a medical procedure. The medical devices and methods utilize a plurality of longitudinal sealed fluid pockets to thermally insulate and cushion an extremity of a limb. The plurality of longitudinal sealed fluid pockets is incorporated in a protective body that is shaped to wrap around the extremity when the medical device is deployed. The protective body has at least one access opening to provide access through the protective body to one or more corresponding portions of the extremity. Access panels may be formed into the protective body to allow portions of the extremity to be covered or uncovered and used with left or right limbs. Other devices and methods are presented.

15 Claims, 9 Drawing Sheets

(56) References Cited

U.S. PATENT DOCUMENTS

| | | | | |
|---|---|---|---|---|
| 6,719,711 B1* | 4/2004 | Islava | ............... | A61F 5/05816 |
| | | | | 128/DIG. 20 |
| 6,892,733 B2 | 5/2005 | Clinton | | |
| 7,540,283 B2* | 6/2009 | Loori | ............... | A61G 10/026 |
| | | | | 128/202.12 |
| 8,646,457 B2* | 2/2014 | Maynard | ............... | A61G 13/10 |
| | | | | 128/877 |
| 2011/0240039 A1* | 10/2011 | Reyes | ............... | A61B 19/088 |
| | | | | 128/853 |
| 2013/0296757 A1* | 11/2013 | Kaphingst | ............... | A61F 5/013 |
| | | | | 602/20 |

* cited by examiner

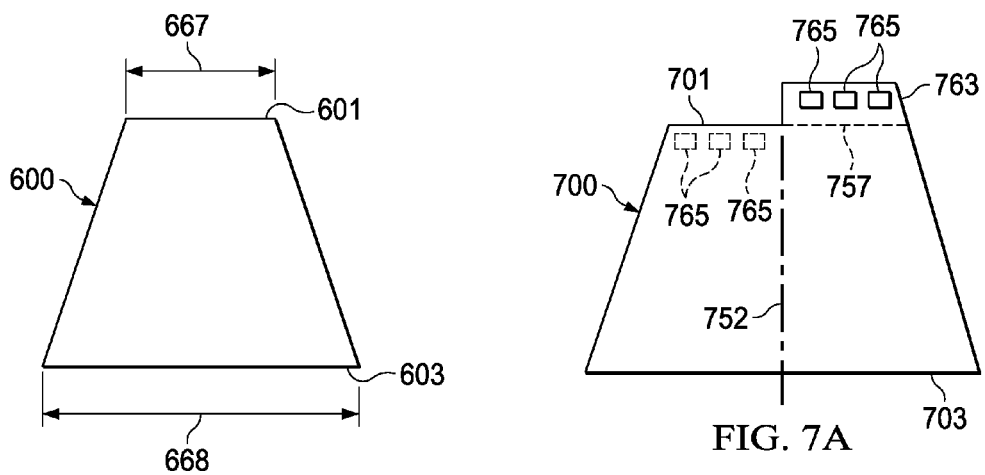
FIG. 6
FIG. 7A
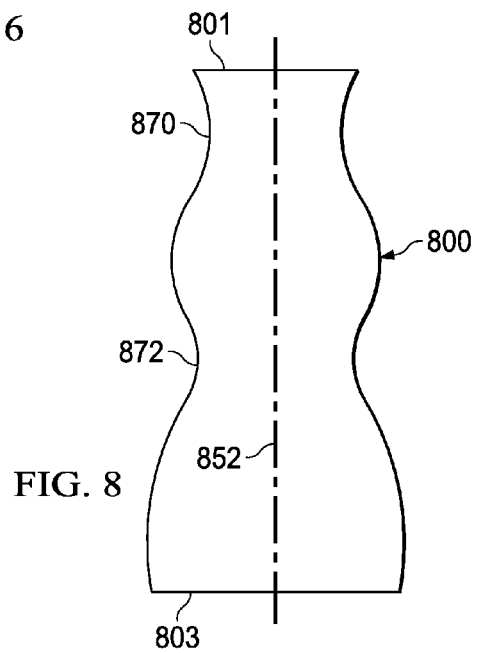
FIG. 8
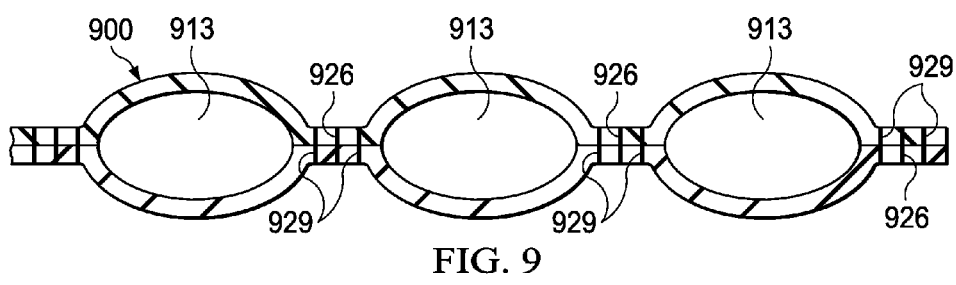
FIG. 9

_US 10,179,062 B2_

MEDICAL DEVICES AND METHODS FOR PROTECTING A LIMB OF A PATIENT DURING A MEDICAL PROCEDURE

TECHNICAL FIELD

The present disclosure relates generally to medical devices for protecting patients during medical procedures, and more particularly, to medical devices and methods for protecting a limb of a patient.

BACKGROUND

During medical procedures, a limb of a patient is often positioned to control its location and to support it. Such efforts help to protect the limb from experiencing injuries, such as nerve damage, open sores, and burns. Limiting movement of a limb's position helps to ensure that medical devices, such as intravenous lines, remain properly positioned in order to interact with the limb. Access to multiple portions of the limb, however, is typically required during medical procedures.

BRIEF DESCRIPTION OF THE DRAWINGS

Illustrative embodiments of the present disclosure are described in detail below with reference to the attached drawing figures, which are incorporated by reference herein.

FIG. 6 is a schematic, plan view of an illustrative embodiment of a medical device for protecting a limb of a patient during a medical procedure;

FIG. 7A is a schematic, plan view of an illustrative embodiment of a medical device for protecting a limb of a patient during a medical procedure;

FIG. 8 is a schematic, plan view of an illustrative embodiment of a medical device for protecting a limb of a patient during a medical procedure; and FIG. 9 is a schematic, cross sectional view of an illustrative embodiment of a medical device for protecting a limb of a patient during a medical procedure.

Figure 1:
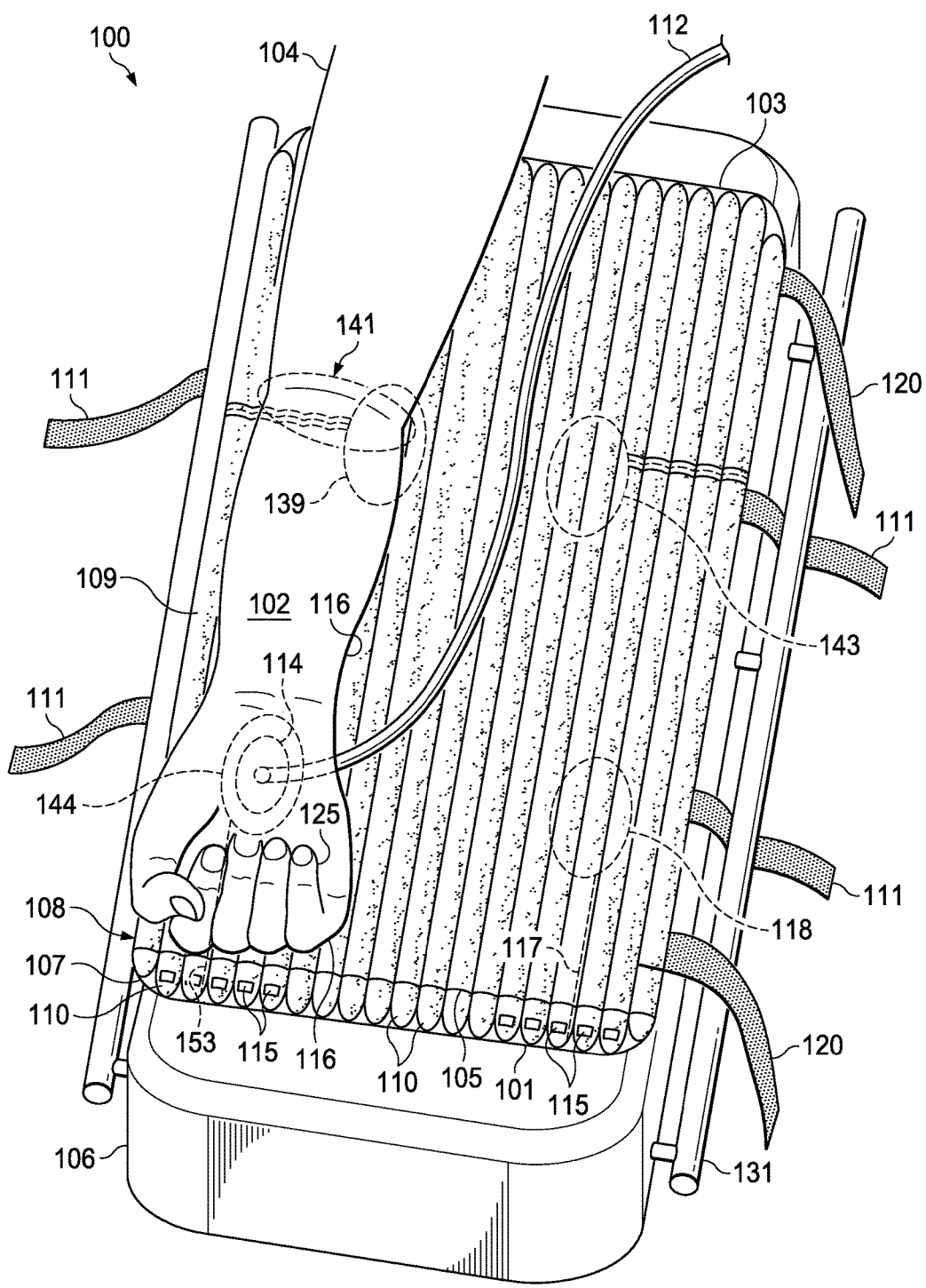
FIG. 1 is a perspective view of a medical device for protecting a limb of a patient during a medical procedure, according to an illustrative embodiment.

The figures described above are only exemplary and their illustration is not intended to assert or imply any limitation with regard to the environment, architecture, design, configuration, method, or process in which different embodiments may be implemented.

DETAILED DESCRIPTION OF THE ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

In the drawings and description that follow, like parts are typically marked throughout the specification and drawings with the same reference numerals or coordinated numerals. The drawing figures are not necessarily to scale. Certain features of the illustrative embodiments may be shown exaggerated in scale or in somewhat schematic form and some details of conventional elements may not be shown in the interest of clarity and conciseness.

The embodiments described herein relate to medical devices and methods for protecting a limb of a patient during a medical procedure. More specifically, medical devices and methods are presented wherein a plurality of longitudinal sealed fluid pockets is utilized to thermally insulate and cushion an extremity of a limb. The plurality of longitudinal sealed fluid pockets is incorporated in a protective body that is shaped to wrap around the extremity when the medical device is deployed. The protective body has at least one access opening to provide access through the protective body to one or more corresponding portions of the extremity. Access panels may be formed into the protective body to allow portions of the extremity to be covered or uncovered. The device may be stored substantially flat. Other devices and methods are presented.

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to". Unless otherwise indicated, as used throughout this document, "or" does not require mutual exclusivity.

As used herein, the term "extremity" refers to any portion of a limb from a point at least somewhat displaced from the patient's torso to its distal end (relative to the torso). For example, and without limitation, an extremity of an arm refers to any portion of the arm located between the portion of the arm near the shoulder to a tip of the arm's longest-extending finger, and more typically between location just above the elbow and the tip of the finger. Similarly, and without limitation, an extremity of a leg refers to any portion of the leg located between a portion of the leg near the groin to a tip of the leg's longest-extending toe and more typically from just above a patient's knee to a tip of the leg's longest-extending toe.

Referring now to the drawings and primarily to FIG. 1, a perspective view is presented of a medical device 100 for protecting a limb 102 of a patient 104 during a medical procedure according to an illustrative embodiment. The medical device 100 is situated between the limb 102 and a support 106. The medical device 100 is shown in an undeployed position, or unsecured position. FIG. 1 depicts the medical device 100 in the context of protecting a right arm of a patient. This depiction is not, however, intended as limiting. Other contexts and associated embodiments are possible (i.e., a right leg, a left arm, and a left leg).

The medical device 100 may be sized from the patient's digits 125 at a first end 101, or distal end, to above a primary joint, e.g., elbow in FIG. 1, at the second end 103, or proximal end (relative to the end of the patient's torso). Protecting the joint is important because there is minimal tissue at the joint and that makes it more prone to injury than other areas. In the example of an arm, the ulnar nerve needs particular protection at the elbow, and the medical device 100 provides the protection.

Figure 2A:
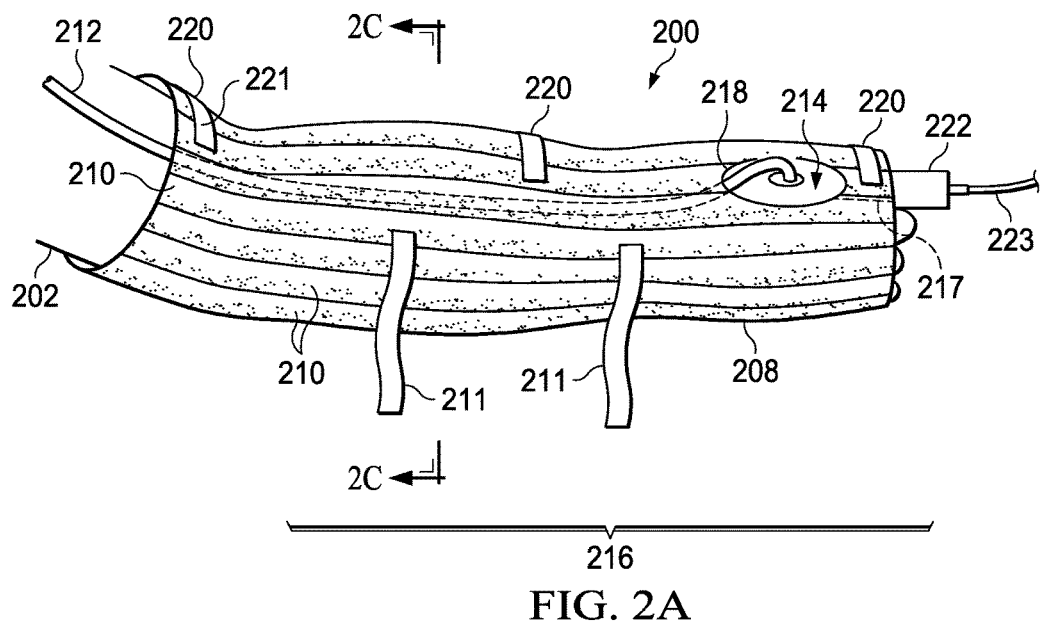
FIG. 2A is a perspective view of an illustrative embodiment of a medical device deployed around an extremity of a limb for protecting the limb during a medical procedure, according to an illustrative embodiment.
Figure 5:
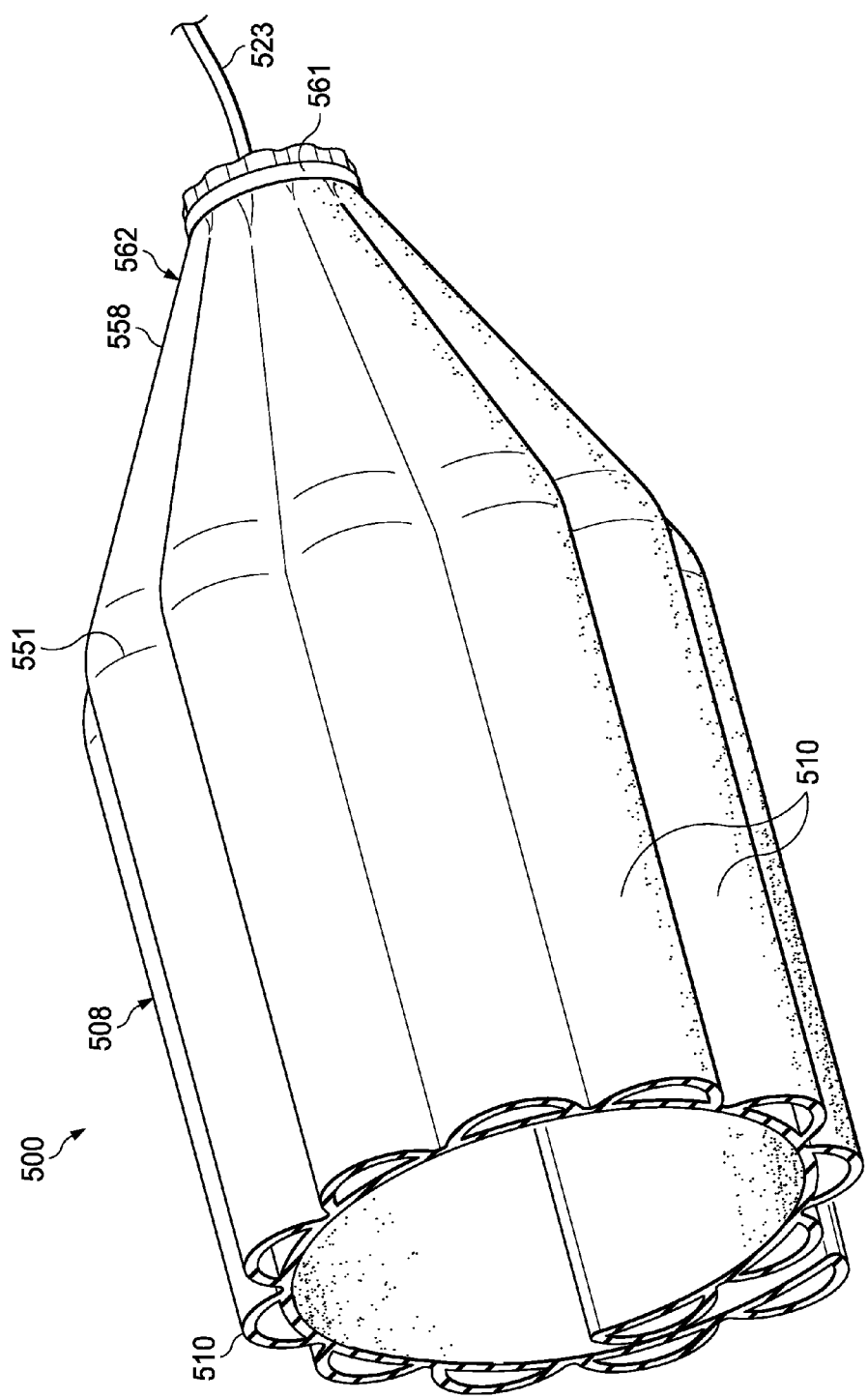
FIG. 5 is a schematic, perspective view of a portion of an illustrative embodiment of a medical device for protecting a limb of a patient during a medical procedure having a selectably closed end.

With respect to the first end 101, the present embodiment of FIG. 1 shows an open-ended configuration with open access to digits 125 when in the deployed, or secured position as shown in FIG. 2A. It should be noted that the distal end 101 may be closed by pulling the end 101 inward about crease 105, which forms a flap 107, over the end of the extremity 116 and securing the flap 107 in position with one or more fasteners 115, e.g. hook-and-loop fasteners. Other embodiments for closing the distal end of the medical device 100 are shown in FIGS. 5 and 7. The first end 101 is selectably closed, e.g., using flap 107, to provide better insulation of the patient's hand or digits, but allowing access to the digits for treatment purposes. It should be understood that aspects of the various embodiments may be combined.

Continuing to reference FIG. 1, the medical device 100 has a protection body 108 that includes a plurality of longitudinal sealed fluid pockets 110, or cannulas. The plurality of longitudinal sealed fluid pockets 110 serve to thermally-insulate and cushion the limb 102. In addition, the plurality of longitudinal sealed pockets 110 provides redundancy in certain embodiments in which each pocket is pneumatically independent of other pockets. In this way, if one of the members of the plurality of sealed fluid pockets 110 ruptures or is defective, it would not impact the others. The sealed pockets 110 may be filled to make the protection body 108 rigid or may be partially filled to allow flexibility of motion while still providing cushion. The thermal insulation qualities of the plurality of sealed pockets 110 are such that additional heat sources are not typically required to maintain adequate warmth of the patient's extremity 116. As such, the sealed fluid pockets 110 substantially maintain the temperature of the patient's limb.

The sealed fluid pockets 110 may be formed with any biocompatible polymer. The sealed fluid pockets 110 are preferably formed to be translucent and at least in some embodiments more specifically formed to be transparent. When translucent, and certainly when transparent, the healthcare provider treating the patient is able to gain some visual information concerning the conditions of the extremity 116 under the medical device 100. In some embodiments, the entire medical device 100 is transparent to allow the healthcare provider to view the entire extremity 116 that would otherwise be covered.

Figure 2B:
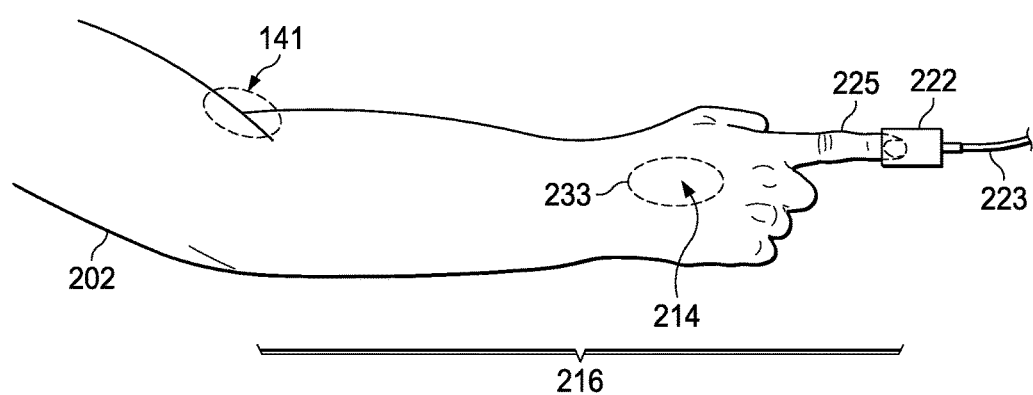
FIG. 2B is a perspective view of the limb of FIG. 2A as positioned therein, but without the medical device.
Figure 2C:
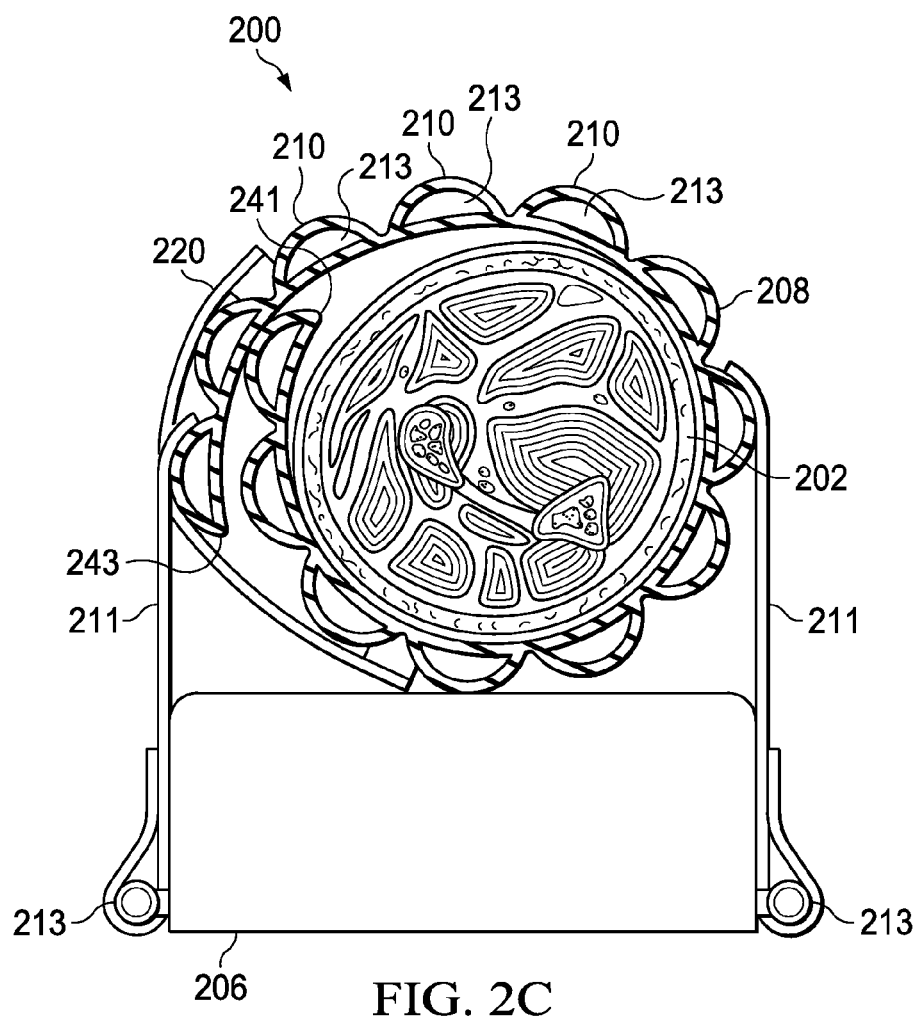
FIG. 2C is a cross-sectional view of the medical device and limb of FIG. 2A taken along line 2C-2C, showing a cross-section shape of a plurality of longitudinal sealed fluid pockets and an arrangement of the plurality of longitudinal sealed fluid pockets around the medical device, according to an illustrative embodiment.

A plurality of securing devices 111, e.g., securing straps, hold the medical device 100 to a portion of the support 106, e.g., to a securing bar 131, (see 211 and 213 in FIG. 2C). Once the medical device 100 is applied to the extremity 116, the medical device 100 is secured relative to the support 106 using the securing devices 111. In this way, the potential for injury to the patient is minimized. The securing devices 111 may be straps with a fastener on the end, such as a buckle, latch, or hook-and-loop fastener (such as a VELCRO brand fastener).

An intravenous line 112 (shown partially with hidden lines) runs between the extremity 116 and the medical device 100 as shown or in some embodiments could be run externally to the medical device 100, e.g., between the protection body 108 and the optional support 106. The intravenous line 112 accesses a portion 114 of an extremity 116 of the limb 102 at or about a first access opening 118 (see also by analogy 218 in FIG. 2A). The first access opening 118 provides a location for at least a portion of the intravenous line 112 to extend through and the medical device 100 may include a perforated slot 117 that can may be torn or cut to allow access to opening 118 and the portion 114. Another common location for the intravenous line 112 to couple with a patient is at the patient's elbow proximate area 141 and an access portion 139 is provided for that purpose. Another access opening 143 is shown so that the medical device 100 may be used on a left extremity. Similarly, in one embodiment, another access opening 144 is provided to access the back of a left hand of an extremity. A perforated slot 153 may be associated with the access opening 144 to provide a way to move an intravenous line to the opening 144 without removing the intravenous line from the patient. In FIG. 1, the portion 114 of the extremity 116 that is coupled to the intravenous line 112 is a backside of a right hand. Again, other portions, however, are possible.

The medical device 100 includes at least one fastener 120 for holding the protection body 108 of the medical device 100 in position about the extremity 116 when the medical device 100 is deployed around the extremity 116. The fastener may be a belt with a hook-and-loop fastener (e.g., VELCRO brand fastener), or a tie, or a buckle arrangement, or any suitable closure device. The fastener 120 allows the protection body 108 to be held in position around the extremity 116 as seen well in FIG. 2C, where the analogous fastener is shown as numeral 220. In one embodiment, the fastener may extend partially around the medical device but over the longitudinal edges or may extend all the way around the deployed medical device 100.

Now referring primarily to FIGS. 2A-2C, and initially to FIGS. 2A and 2B, a perspective view is presented of an illustrative medical device 200 deployed around an extremity 216 of a limb 202 for protecting the limb 202 during a medical procedure according to an illustrative embodiment. FIG. 2B shows the limb 202 as otherwise positioned in FIG. 2A, but without the medical device 200. While the limb 202 of FIGS. 2A-2B is depicted as being a right arm, this depiction is not intended as limiting. Embodiments of the medical device 200 may be directed to other limbs (i.e., a right leg, a left arm, a left leg). The medical device 200 illustrated in FIG. 2A is analogous to the medical device 100 illustrated in FIG. 1. Features analogous to both FIG. 2A and FIG. 1 are generally related via coordinated numerals that differ in increment by a hundred.

The medical device 200 includes a protection body 208 formed from a translucent, biocompatible polymer comprising a plurality of longitudinal sealed fluid pockets 210. Translucent means that light travels through the material at least at some level to allow some features to be seen by the healthcare provider from a point exterior to the medical device 200. In some embodiments, a light source may be directed through the material to more clearly view a portion of the patient through the polymer. In some embodiments, the polymer is transparent to allow features under the medical device 200 to be clearly seen through the material. The protection body 208 is formed with a plurality of longitudinal sealed fluid pockets 210.

The longitudinal sealed fluid pockets 210 define internal chambers (see 213 in FIG. 2C) whose longitudinal orientation is substantially parallel to the limb 202. Such orientation imparts flexibility to the protection body 208 and enables the medical device 200 to be wrapped around the extremity 216 with minimal mechanical resistance. It should be understood that the size and shape of the internal chambers may vary. For example, while half-moon shapes are shown in the cross section of FIG. 2C, circular shapes, reverse half-moons, squares, etc., might be used as well. One or both of the surfaces may be shaped. The longitudinal sealed fluid pockets may be filled with a fluid until tight to the touch and thereby fairly rigid or may be only partially filled to allow more flexibility while still cushioning the extremity. It should be noted that FIG. 2C is for illustrative purposes only and, while not explicitly shown, the weight of the extremity would flatten the portion of the sealed fluid pockets 210 between the extremity and a support 206. In addition, while some air space may appear between a portion of the medical device 200 and the extremity at the center of the drawing, in actual practice, there would be little or no space between the medical device 200 and a skin portion of the extremity 216.

FIG. 2C provides a cross-sectional view of the medical device 200 and limb 202 of FIG. 2A, showing an illustrative, schematic cross-sectional shape of the internal chambers 213 and an arrangement of the longitudinal sealed fluid pockets 210 on the protection body 208, according to an illustrative embodiment. The longitudinal sealed fluid pockets 210 may be filled with any of numerous fluids. As used herein, "fluids" means a substance (as a liquid or gas) tending to flow or conform to the outline of its container. Examples of fluids that might be used include air, saline, silicone oil, etc. Such fluids may function to thermally-insulate the limb 202 from ambient surroundings, dampen impacts made to the limb 202, and to support and distribute a weight of the limb 202. Other fluid functions are possible.

In some embodiments, the translucent, biocompatible polymer includes a transparent polymer. In such embodiments, the transparent polymer enables a clear view through the protection body 208 for observing the extremity 216 with clarity. Such observation typically also includes monitoring one or more other medical devices or conditions interacting with the extremity 216.

The protection body 208 is formed with a first access opening 218 and a perforated slot 217. The protection body 208 is configured to surround the extremity 216 of the limb 202 when in a deployed position like in FIG. 2A. The first access opening 218 provides access through the protection body 208 to a first portion 214 of the extremity 216 and when open slot 217 allows a positioned intravenous line 212 to access the opening 218 without removing the intravenous line 212. In FIG. 2A, the first portion 214 of the extremity 216 is a backside of a hand, but other locations might be used, such as an elbow. FIG. 2B highlights the first portion 214 of the extremity 216 via a broken line 233. The broken line approximately represents a projection of the first access opening 218 onto the extremity 216 of the limb 202 in the deployed position. Again, it will be appreciated that the first access opening 218 may be formed elsewhere within the protection body 208 to provide access to other portions of the extremity 216. For example, returning to FIG. 1, access openings 139 may be provided to access a portion 141 of the extremity and gain access to the venous system proximate the elbow.

The medical device 200 may also include an access panel (see 324 of FIG. 3A) proximate the first access opening 218 for covering the first access opening 218 when the protection body 208 is in at least a storage position, or un-deployed position. The first access panel 324 is typically opened or removed after the protection body 208 leaves the storage position and enters the deployed position. FIG. 2A shows the protection body 208 without the first access panel 324, allowing an intravenous line 212 to interact with the first portion 214 of the extremity 216. Similarly, additional or alternatively located access openings and panels may be provided; for example, access panel 139 in FIG. 1 (325 in FIG. 3A) covers an access opening (327 in FIG. 3A) proximate the patient's elbow. Discussion herein concerning first access panel 324 and access opening 318 applies analogously to the access opening 327 and panel 325, and access opening 319. Both access openings 327 in FIG. 3A may have an associated perforated slot 354 that may be torn or cut to allow an intravenous line to access the opening 327 without removal from the patient.

In some embodiments, the first access panel 324 is removably coupled to the protection body 208 by a perforated, sealed border. In such embodiments, the first access panel 324 may be severed from the protection body 208 (e.g., by tearing, cutting, etc.) in order to uncover the first portion 214 of the extremity 216 while not deflating the internal chambers 213. In other embodiments the first access panel 324 is coupled to the protection body by a hinge (e.g., welded joint) and may just be opened as needed to gain access. In still another embodiment, the hinge may be perforated to allow hinging operation or removal. In these embodiments, the first access panel 324 may be rotated along the hinge to uncover the first portion 214 of the extremity 216. Such rotation allows the first access panel 324 to be opened and closed, allowing convenient access to the first portion 214 of the extremity 216 as needed. The rotated first access panel 324 may be taped open, if desired, to keep the first access opening 218 uncovered. Alternatively, the first access panel 324 may be severed from the protection body 208 along the hinge by tearing, cutting, ripping, and so forth. In embodiments where the first access panel 324 is coupled by the hinge, the first access panel 324 may be secured, when closed, by an interference fit with the protection body 208 other selectably closeable arrangement. Other temporary closing arrangements, e.g., a hook-and-loop connection, might be included.

The medical device 200 includes at least one fastener 220 associated with the protection body 208 for holding the protection body 208 in the deployed position about the extremity 216. The at least one fastener 220 is operable to help the protection body 208 fit conformally to the extremity 216 and may secure other medical devices, such as the intravenous line 212, to the extremity 216. In some embodiments, the at least one fastener 220 comprises a hook-and-loop (e.g., VELCRO brand closure) closure arrangement using a strap 221 and a receiving portion or pad. As shown best in FIG. 3A, a strap 321 may releasably couple with a receiving portion 323. In another embodiment, the at least one fastener 220 may be a strap with an adhesive covered by a removal backing.

As shown in FIG. 2C, the protection body 208 has a first longitudinal edge 241 and a second longitudinal edge 243. The first longitudinal edge 241 is overlapped by the second longitudinal edge 243 as shown. The degree of overlap may vary depending on desired overlap and size of the patient's arm. A portion may also be removed in some embodiments as mentioned in connection with FIG. 7 below. Once overlapped, the fastener 220 may be used to hold the overlapped position about the extremity. It will be appreciated that FIG. 2C is a schematic and in application in some embodiments the sealed fluid pockets 210 between the patient and the support would deflect or widen in this view thereby assisting with weight distribution.

It will be appreciated that the protection body 208 of the medical device 200 may be formed with access openings in addition to the first access opening 218. In some embodiments, the protection body 208 is formed with a second access opening (e.g., by analogy openings 319 and 325 in FIG. 3A) that provides access through the protection body 208 to a second portion of the extremity 216. In other embodiments, the medical device 200 includes a second access panel proximate the second access opening for covering the second access opening when the protection body 208 is in at least the storage position. Like the first access panel 324, the second access panel (e.g., covering opening 319) is typically removed or opened after the protection body 208 leaves the storage position to enter the deployed position. In still further embodiments, the second access panel is removably coupled to the protection body by a perforated, sealed border. In such embodiments, the second access panel may be severed from the protection body 208 (e.g., by tearing, cutting, etc.) in order to uncover the second portion of the extremity 216.

Figure 3A:
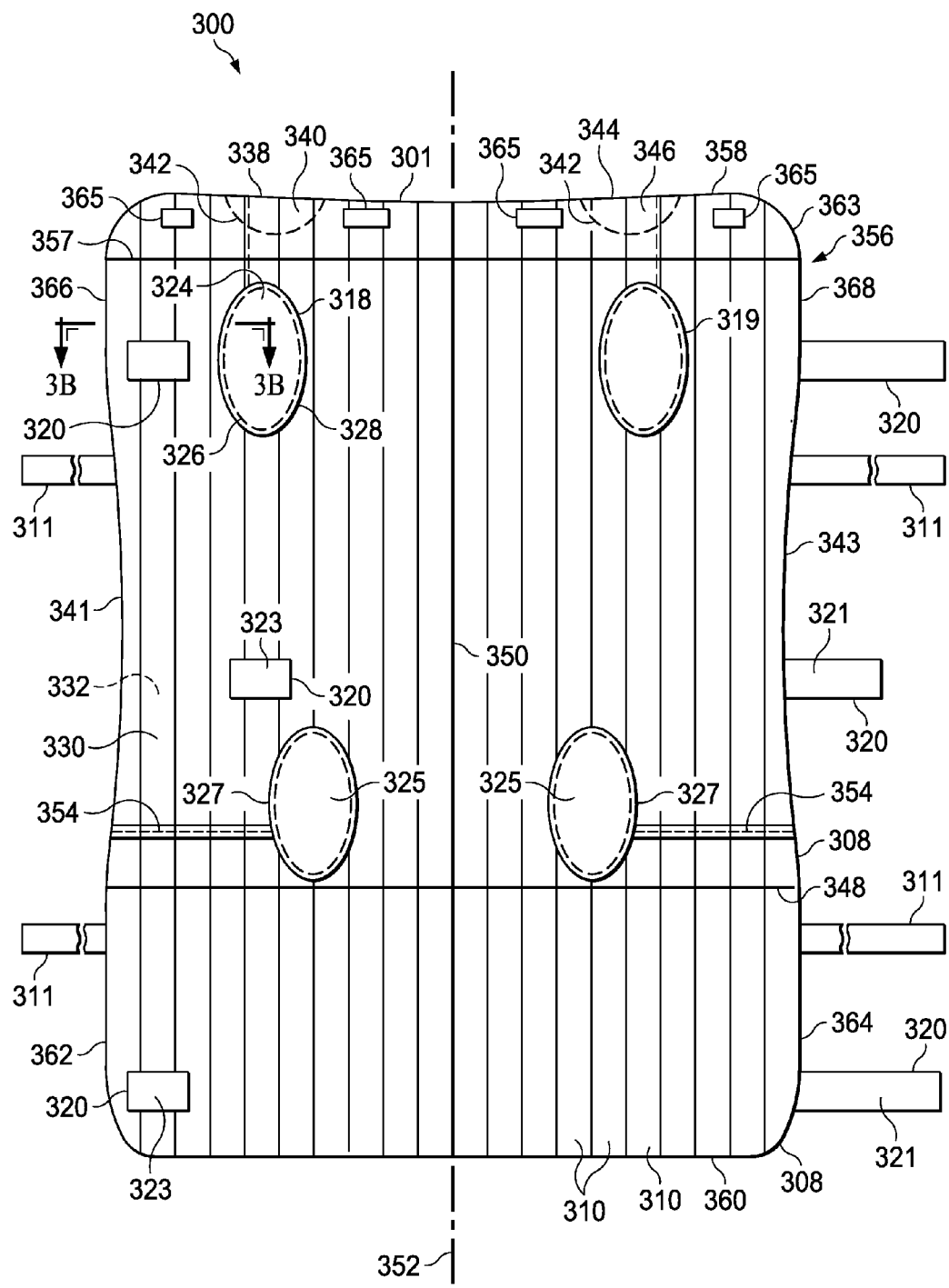
FIG. 3A is a plan view of an illustrative embodiment of a medical device for protecting a limb of a patient during a medical procedure, in an open position, according to an illustrative embodiment.

In some embodiments, the protection body 208 is formed with a first access opening and a second access opening on the opposite side of a centerline (by analogy 352 in FIG. 3A). In this fashion the same medical device may be used on a right limb or left limb without requiring different devices. The unused access opening would typically remain covered by a corresponding access panel.

The protection body 208 may also be formed with an open distal end allowing immediate access to the patient's digits, but may also be formed with access openings that correspond to digit access openings (see 338 and 344 of FIG. 3A). In still other embodiments, e.g., FIG. 5, the distal end may be closed, but an access opening (analogous to 318) may be provided to provide access to the patient's digits. In other embodiments, the distal end may be selectably closed, but then opened for access. Such openings or access may enable monitoring devices to interact with digits of the extremity 216. For example, and without limitation, FIG. 2A shows an oximeter 222 with lead 223 coupled to a finger of the extremity 216. However, medical devices besides monitoring devices may be used with the digit access openings or open end. Access openings for digits are described further in relation to FIG. 3A. It should be noted that FIG. 2A presents an illustrative embodiment having a substantially open end that provides access to the patient's digits 225, but other embodiments, e.g., FIG. 5 below, may include a closure to further maintain heat in the patient's extremity.

Now referring primarily to FIG. 3A, a plan view is presented of a medical device 300 for protecting a limb of a patient during a medical procedure, in an open or undeployed position, according to an illustrative embodiment. The plan view may be substantially a rectangle as shown or may have a taper from the distal end to the proximal end as shown in FIG. 6. Still other shapes are possible (see, e.g., FIGS. 7 and 8). The open position may correspond to the storage position of the medical device 300 and, due to space-efficient occupation of volume, may also be a shipping position. The medical device 300 illustrated in FIG. 3A is analogous to the medical device 200 illustrated in FIG. 2A. Features common to both FIGS. 2A and 3A are generally related via coordinated numerals that differ in increment by a hundred. The medical device 300 has a distal end 301, proximal end 360, first longitudinal edge 341, and a second longitudinal edge 343.

FIG. 3A shows the first access panel 324 covering the first access opening 318. The first access panel 324 is removably coupled to the protection body 308 via a perforated border or line 326. The protection body 308 has a seal outboard of the perforated border 326 to keep the fluid pockets 310 from deflating, or causing a fluid leak, after the first access panel 324 is removed. The location of an analogous second access opening 319 is shown with broken lines. The second access opening 319 would be for use on the opposite limb. Again, the access openings 327 and access panels 325 are analogous to those presented but are positioned to access the patient's elbow.

Figure 3B:
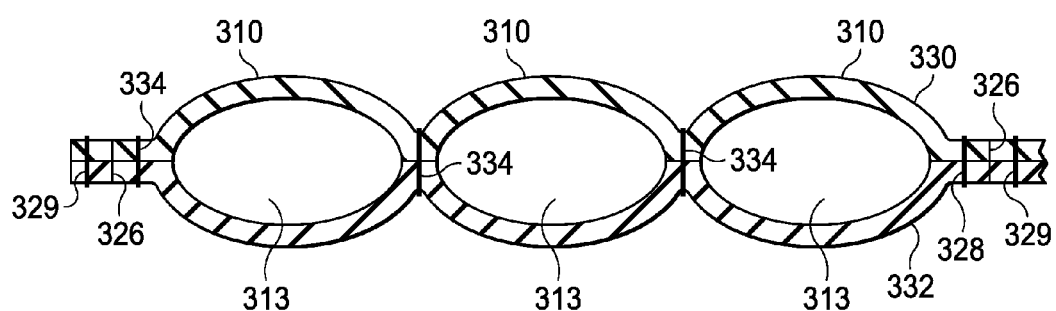
FIG. 3B is a cross-sectional view of a portion of the medical device of FIG. 3A, showing placement of a perforated border relative to a seam of a protective body.

A schematic cross-sectional view is presented in FIG. 3B of a portion of the medical device 300, showing placement of the perforated border 326 relative to a seam 328 and seal 329 of the protective body 308. The seam 328 defines the first access opening 318 within the protective body 308 and may be formed by attaching (e.g., welding, fusing, etc.) a first translucent, biocompatible polymer layer 330 to a second translucent, biocompatible layer 332. As illustrated in FIG. 3B, seams 328, 334 may also serve cooperatively to form the internal chambers 313 that define the plurality of longitudinal sealed fluid pockets 310.

In some embodiments, the first access panel 324 is removably coupled to the protection body 308 by a hinge, e.g., a weld, that allows that access panel to move from a closed position to an open position. In some embodiments, the first access panel 324 optionally may be severed from the protection body 308 along the hinge (e.g., by tearing, cutting, ripping, etc.). The hinge may include perforations to facilitate tearing.

Figure 4:
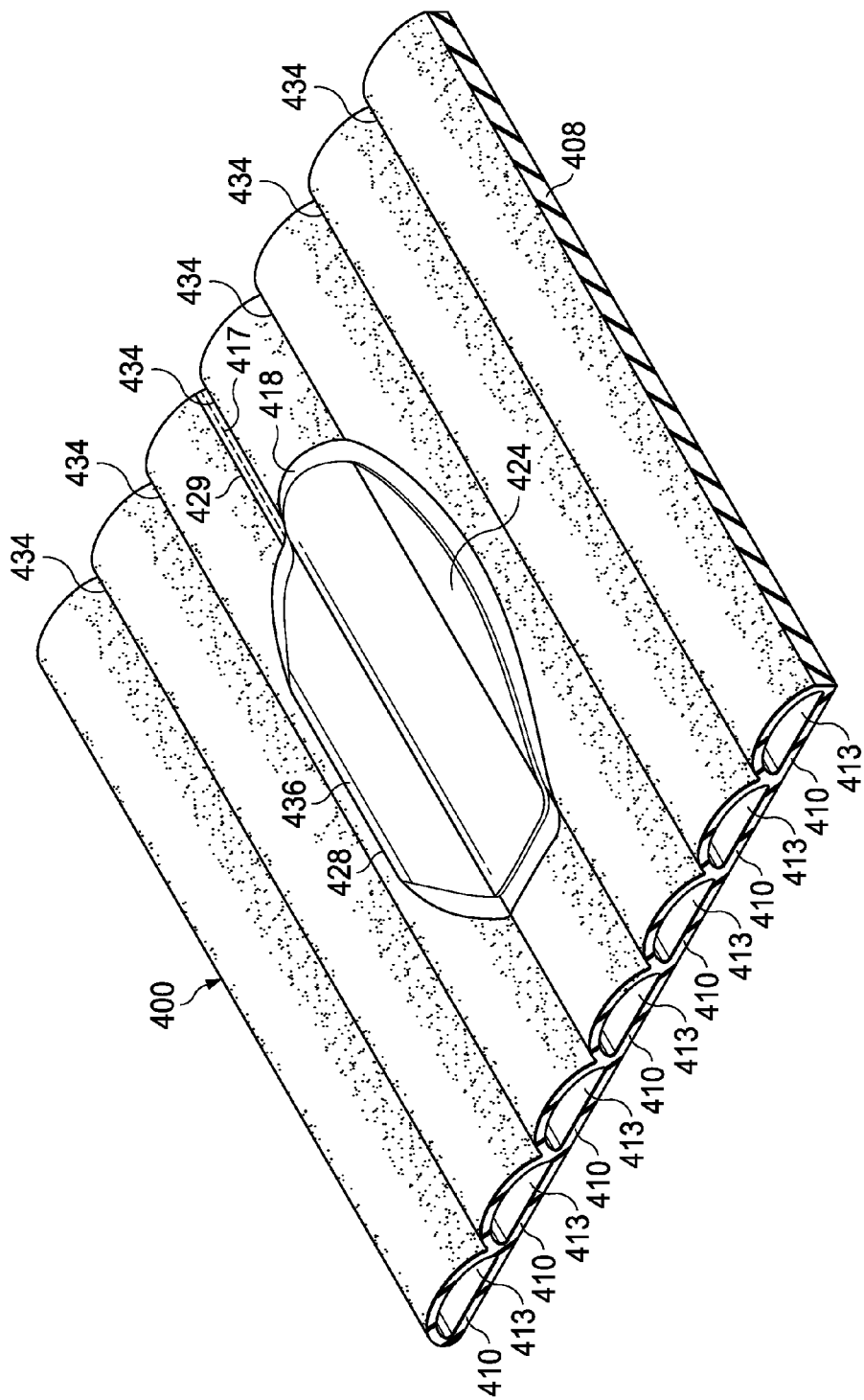
FIG. 4 is a perspective view of a first access panel removably coupled to a protection body by a hinge.

FIG. 4 presents an illustrative embodiment of a portion of a medical device 400 analogous in most respects to other medical devices herein. The view of FIG. 4 shows the medical device 400 having a first access panel 424 removably coupled to a protection body 408 by a hinge 436. The hinge 436 may be formed as a continuous flap from the protection body 308 or an attached member that is attached by weld, glue, or other means. In addition, a portion of the hinge may be perforated for removal. The view in FIG. 4 shows internal chambers 413 of the longitudinally sealed pockets 410. Features analogous to both FIGS. 3A and 4A are related via coordinated numerals that generally differ in increment by a hundred. The first access panel 424 is depicted as freely-movable, using a portion of a seam 428 for the hinge 436. Other types of hinges, however, are possible. Liberation of the first access panel (i.e., to allow rotation about the hinge 436) may in some embodiments require first severing a partially-encompassing perforated border. In some embodiments, the first access panel 424 is secured, when closed, by an interference fit with the protection body 408. A perforated slot 417 may be included.

The slot 417 may have seals or seams 429 on each side so that the medical device will not leak when the perforation is torn or cut. Other fastening arrangements might be used.

Now referring again to FIG. 3A, in some embodiments, the protection body 308 is formed with a first digit access opening 338 positioned such that, when the protection body 308 is in the deployed position, the digit access opening 338 exposes a third portion of the extremity proximate the patient's digits. The opening 338 would be used to gain access (or additional access) to a portion of a patient's extremity, e.g., a digit, preferably on a left limb (left arm or left leg). In some embodiments, the protection body 308 includes a digit access panel 340 proximate the access opening 338 for covering the digit access opening 338 when the protection body 308 is in at least the storage position. Perforations 342 may be formed into the protection body 308 to enable removal of the digit access panel 340 in a manner analogous to those previously described.

In some embodiments, the protection body 308 alternatively or in addition is formed with an additional access opening (second digit access opening) 344 positioned such that, when the protection body 308 is in the deployed position, the additional access opening 344 exposes a fourth portion of the extremity. The additional access opening 344 would be used to gain access to a portion of a patient's extremity, e.g., a digit, preferably on a right limb (right arm or right leg). In further embodiments, the protection body 308 includes an additional access panel 346 (second digit access panel) proximate the additional access opening 344 for covering the access opening 344 when the protection body 308 is in at least the storage position. Perforations 342 may be formed into the protection body 308 to enable removal of the access panel 346.

In some embodiments, the protection body 308 includes at least one lateral joint or crease 348. The lateral joint 348 may be formed as a welded portion or creased portion. The at least one lateral joint 348 is arranged laterally and a position along the protection body 308 such that, when the protection body 308 is in the deployed position, the at least one lateral joint 348 facilitates enhanced lateral flexure of the medical device 300 at a predetermined location. For example, and without limitation, the predetermined location could correspond to a wrist joint of an arm to allow movement of a hand or an elbow area to allow movement of the arm or to an elbow area to allow the arm to move at the elbow. Other predetermined locations, however, are possible.

In some embodiments, the protection body 308 includes a lateral crease 357 that can be used to pull up the distal end over the patient's digits for form a closure at the distal end. The portion of the protection body 308 distal to the crease 357 forms a flap 363. Coordinated fasteners 365 may be added to the flap 363. In another embodiment, the flap 363 may have different lengths to facilitate closure as suggested in FIG. 7 described below.

In some embodiments, the protection body 308 includes at least one longitudinal hinge 350 or flexing zone. The at least one longitudinal hinge 350 is arranged along the protection body 308 such that, when the protection body 308 is held by the at least one fastener 320 in the deployed position, the at least one longitudinal hinge 350 is oriented substantially parallel to the extremity. For example, and without limitation, the at least one longitudinal hinge 350 could be located on a centerline 352 of the protective body 308 to improve folding of the medical device 300. When included, the longitudinal hinge 350 is typically placed on the patient's extremity with the hinge 350 between the patient's torso and the extremity when in the deployed position.

In an illustrative embodiment, the protection body 300 may be patterned into a symmetrical shape or numerous other shapes, rectangular, tapered, irregular but symmetrical, etc., such as that shown in FIG. 3A or FIG. 6, 7A, or 8. Symmetry facilitates use with either left-sided limbs or right-sided limbs. A first side (109 in FIG. 1) of the protection body 300 is placed proximate the extremity of the limb and secured with the at least one fastener 320. When used with a right-sided limb, the centerline 352 is placed on a torso-side of the right limb, and when used with a left-sided limb, the centerline 352 is placed on a torso-side of the left limb. In the former, the access opening 318 will be over the top of the hand and in the latter the access opening 319 will be over the top of the hand. Thus, the same medical device 300 is equally applicable to left-sided limbs or right-sided limbs.

Other access openings may also be formed symmetrically on the protection body 308 to accommodate left-sided limbs or right-sided limbs. For example, and without limitation, the first digit access opening 338 and the second digit access opening 344 may be mirrored in shape and placement relative to the centerline 352, as shown in FIG. 3A. Such shape and placement may be enable access to digits of the limb, regardless of whether the limb protected by the medical device 300 is left-sided or right-sided. Other symmetrical shapes and placements are possible. The deployed protection body 308 has a first, or distal, end 358 (first end) and a second, or proximal end 360.

According to an illustrated embodiment, a method for protecting a limb of a patient during a medical procedure includes the step of providing a medical device for protecting the limb of the patient. The medical device may be stored in a flat position when un-deployed and be suitable for use with a right or left limb. As used herein, flat means less than less than less than half of its deployed height and in some embodiments less than 40% of its deployed height. The medical device includes a protection body formed from a translucent, biocompatible polymer including a plurality of longitudinal sealed fluid pockets containing a fluid. The protection body is configured to surround an extremity of the limb when in the deployed position and is formed with a first access opening that provides access through the protection body to a first portion of the extremity where an intravenous line may be administered. The medical device may also include a first access panel proximate the first access opening for covering the first access opening at least when the protection body is in a storage position. The medical device includes at least one fastener associated with the protection body for holding the protection body in the deployed position about the extremity.

The method also includes the step of disposing the extremity onto a first surface of the medical device. The method involves the step of folding the medical device longitudinally about the extremity to substantially surround a portion of the extremity. The method also involves the step of securing the medical device about the extremity using the at least one fastener, e.g., a hook-and-loop strap and pad, and the step of moving the first access panel to uncover the first access opening, thereby providing access to the first portion of the extremity.

The method may also include using a medical device having a lateral crease formed near the distal end of the medical device whereby a flap is formed, and then folding the flap over digits of the patient and securing the flap to a receiving portion of the medical device. In this way, the limb may be kept warmer.

In some embodiments, the medical device further includes a digit access opening and a digit access panel. The digit access panel is located proximate the digit access opening for covering the digit access opening when the protection body is in at least the storage position. In such embodiments, the method further includes the step of moving the digit access panel to uncover the digit access opening, thereby providing access to a digit of the extremity. In still other embodiment, the distal end of the medical device is closed or substantially closed about the patient's hand (or foot) to help further insulate the extremity. In such case, the digit access panel provides selectable access to the patient's digit(s).

Referring now primarily to FIG. 5, a portion of a illustrative embodiment of a medical device 500 that is analogous in many respects to the other medical devices herein, but includes end closure or closure portion 562 at the distal end 558. Thus, the medical device includes a protection body 508 that includes a plurality of longitudinal sealed fluid pockets 510. The closure portion 562 may include a crease or joint 551. In this embodiment, the closure portion 562 comprises portions of the plurality of longitudinal sealed fluid pockets 510 configured to converge with a general frustoconical shape, or funnel-like shape, and be secured by a securing device 561, e.g., a cincture strap, tape, hook-and-loop strap or tab, or the like. In this way, the patient's digits may be inside an interior formed by the medical device 500 and thereby remain thermally protected. This arrangement still allows a lead 523 to access an interior portion proximate the patient's digit through an opening at the distal end.

When using the medical device 500 of FIG. 5, it would be used analogously to those previously presented medical devices except the distal end is closed about the patient's digits. Access to digits is through an access panel or by loosening the securing device 561 to provide at least a temporary opening on the distal end. The medical 500 allows the patient's extremity to be heated by the patient's own body heat—convection heat—without requiring an external heater.

Referring now to FIG. 6, a plan view of an illustrative embodiment of a medical device 600 is presented that is analogous to those previously presented in most respects. In this embodiment, the medical device 600 is clearly formed with a trapezoid shape. Thus, the width 667 of the distal end is less than the width 668 of the proximal end. Again, other shapes are possible.

Figure 7B:
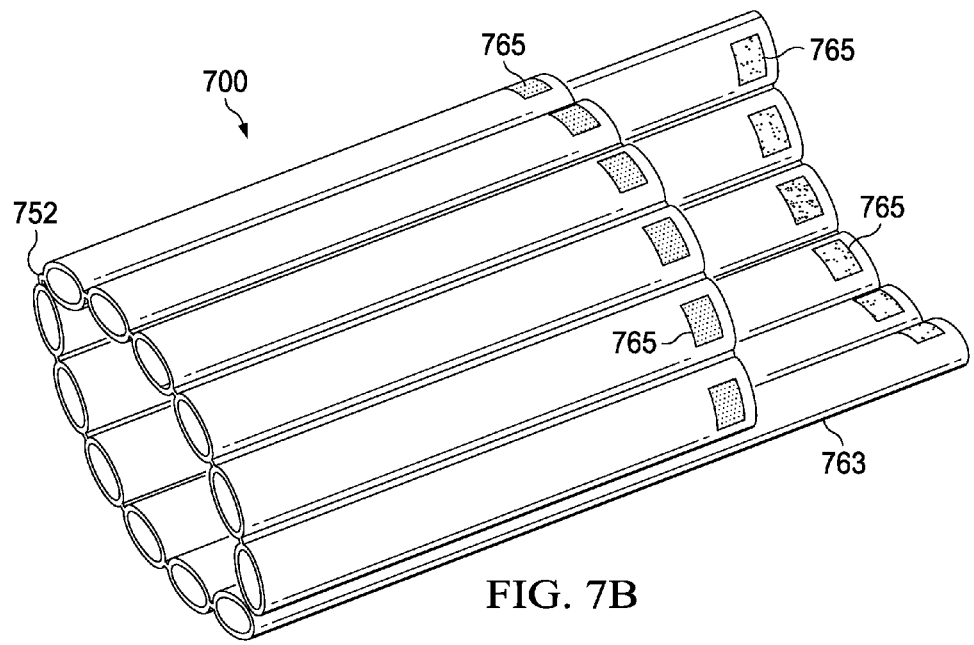
FIG. 7B is a schematic, perspective view of the medical device of FIG. 7A folded about its centerline.
Figure 7C:
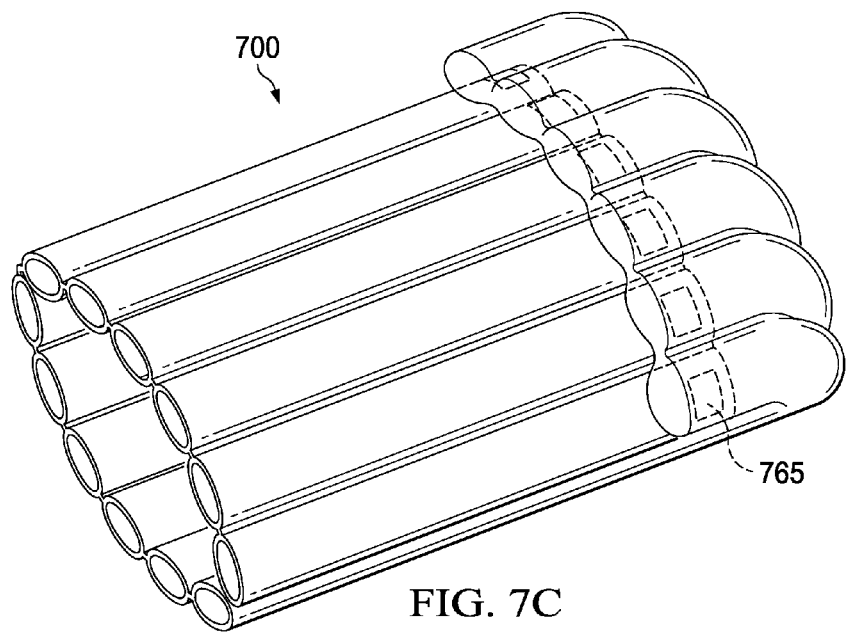
FIG. 7C is a schematic, perspective view of the medical device of FIGS. 7A and 7B with the flap folded and secured.

Referring now to FIG. 7A, a plan view of an illustrative embodiment of a medical device 700 is presented that is analogous to those previously presented in most respects. In this embodiment, the medical device 700 is formed with a crease 757 forming a flap 763 at the distal end 701. The crease 757 in this embodiment is only formed one side of the centerline 752. In this way the flap 763 extends further than the distal end on the other side of the centerline and allows for an overlap that then may be secured using coordinated fasteners 765. The medical device 700 is shown folded about the centerline 752 in FIG. 7B and then with the fasteners 765 securing the flap in FIG. 7C.

Referring now to FIG. 8, a plan view of an illustrative embodiment of a medical device 800 is presented that is analogous to those previously presented in most respects. The medical device 800 has a distal end 801 and a proximal end 803. In this embodiment, the medical device 800 has a symmetrical shape about the centerline 852 with a first narrowing portion 870 and a second narrowing portion 872. In one embodiment, the first narrowing portion 870 and a second narrowing portion 872 in plan view cause the medical device 800 to loosely resemble in shape an hourglass. The overall plan view may be rectangular, trapezoidal, or some other shape. In one embodiment, the first narrowing portion 870 allows less width at a patient's wrist and the second narrowing portion 872 provides less width at the patient's elbow for a better fit of the medical device 800.

Referring now to FIG. 9, a cross section of a portion of an illustrative embodiment of a medical device 900 is presented that is analogous to those previously presented in most respects. In the cross section, the layers 930 and 932 are shown forming internal chambers 913. To form the chambers 913, in between each chamber, two pneumatic seals 929 are formed with a perforated border or line 926 between the seals 929. In this way, the healthcare provider can size the medical device 900 for a particular patient by tearing or cutting along the perforation 926. Thus, for example, an adult size medical device 900 may be readily sized for a child.

According to an illustrative embodiment, a medical device of the type described herein includes a plurality of longitudinal sealed fluid pockets that are pneumatically sealed independent pockets whereby deflation of one of the plurality of longitudinal sealed fluid pockets does not deflate other members of the plurality of longitudinal sealed fluid pockets. This may allow the medical device to be readily sized. For example, one or more the perforations may be torn to make the medical device sized to a smaller size.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order or simultaneously where appropriate. Where appropriate, aspects of any of the examples described above may be combined with aspects of any of the other examples described to form further examples having comparable or different properties and addressing the same or different problems.

It will be understood that the above description of the embodiments is given by way of example only and that various modifications may be made by those skilled in the art. The above specification, examples, and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A medical device for protecting a limb of a patient during a medical procedure, the medical device comprising:
 a protection body formed from a translucent, biocompatible polymer;

the protection body comprising a plurality of longitudinal sealed fluid pockets containing a fluid, wherein the plurality of longitudinal sealed fluid pockets comprises at least three longitudinal sealed fluid pockets;

wherein the protection body is configured to surround an extremity of the limb when in a deployed position, with the protection body adapted to surround the limb when deployed;

the protection body formed with a first access opening adapted to access a first portion of the extremity;

a first access panel proximate the first access opening for covering the first access opening when the protection body is in at least a storage position;

at least one fastener associated with the protection body for holding the protection body in the deployed position about the extremity;

wherein the protection body has a distal end and a proximal end, and wherein the medical device has a trapezoidal shape in plan view when the protection body is in a storage position;

wherein the protection body is formed with a second access opening adapted to access a second portion of the extremity;

wherein the protection body is formed with a third access opening positioned such that, when the protection body is in the deployed position and surrounds a left limb, the third access opening exposes a digit of the left limb;

wherein the protection body is formed with a fourth access opening positioned such that, when the protection body is in the deployed position and surrounds a right limb, the fourth access opening exposes a digit of the right limb;

further comprising a second access panel proximate the second access opening for covering the second access opening when the protection body is in at least the storage position;

further comprising a third access panel proximate the third access opening for covering the third access opening when the protection body is in at least the storage position;

further comprising a fourth access panel proximate the fourth access opening for covering the fourth access opening when the protection body is in at least the storage position;

a lateral crease forming a flap proximate a distal end;

a plurality of fasteners coupled to the flap for closing the flap around a portion of the patient when in the deployed position; and wherein the at least one fastener comprises a hook-and-loop closure.

2. The medical device of claim 1, wherein the first access panel is removably coupled to the protection body by a perforated border, and further comprising a perforation extending from a distal end of the medical device to the first access opening.

3. The medical device of claim 1, wherein the first access panel is removably coupled to the protection body by a hinge.

4. The medical device of claim 3, wherein the first access panel is secured, when closed, by an interference fit with the protection body.

5. The medical device of claim 1, wherein the fluid comprises air.

6. The medical device of claim 1, wherein the translucent biocompatible polymer comprises a transparent polymer.

7. The medical device of claim 1, further comprising a plurality of securing devices coupled to an outer portion of the medical device for securing the medical device relative to a support.

8. The medical device of claim 7, wherein the securing devices comprise a plurality of securing straps.

9. The medical device of claim 1, wherein the medical device in plan view when in a storage position has a first narrowing portion, wherein the protection body has a portion on each side of a narrowing portion that is wider than the first narrowing portion.

10. The medical device of claim 1, wherein the plurality of longitudinal sealed fluid pockets comprise pneumatically sealed independent pockets whereby deflation of one of the plurality of longitudinal sealed fluid pockets does not deflate other members of the plurality of longitudinal sealed fluid pockets.

11. The medical device of claim 10, further comprising a plurality of perforations formed between pockets of the plurality of longitudinal sealed fluid pockets whereby one or more of the plurality of perforations may be torn to make the medical device sized to a smaller size.

12. The medical device of claim 1, wherein the protection body comprises:
at least one lateral joint; and
wherein the at least one lateral joint is arranged along the protection body such that, when the protection body is in the deployed position, the at least one lateral joint enables flexure of the medical device about the at least one lateral joint.

13. The medical device of claim 1, wherein the protection body comprises:
at least one longitudinal hinge;
wherein the at least one longitudinal hinge is arranged along the protection body such that, when the protection body is held by the at least one fastener in the deployed position, the at least one longitudinal hinge is oriented substantially parallel to the extremity; and
and wherein the protection body does not surround portions of the patient's body other than the limb.

14. The medical device of claim 1, wherein the plurality of longitudinal sealed fluid pockets are configured to converge and form a frustoconical shape at a proximal end.

15. A medical device for protecting a limb of a patient during a medical procedure, the medical device comprising:
a protection body formed from a translucent, biocompatible polymer comprising a plurality of longitudinal sealed fluid pockets containing a fluid, the protection body configured to surround an extremity of the limb when in a deployed position, the protection body formed with a first access opening adapted to access a first portion of the extremity;
a first access panel proximate the first access opening for covering the first access opening when the protection body is in at least a storage position;
at least one fastener associated with the protection body for holding the protection body in the deployed position about the extremity;
wherein the protection body has a distal end and a proximal end;
wherein the protection body is formed with a second access opening adapted to access a second portion of the extremity;
wherein the protection body is formed with a third access opening positioned such that, when the protection body is in the deployed position and surrounds a left limb, the third access opening exposes a digit of the left limb;

wherein the protection body is formed with a fourth access opening positioned such that, when the protection body is in the deployed position and surrounds a right limb, the fourth access opening exposes a digit of the right limb;

a second access panel proximate the second access opening for covering the second access opening when the protection body is in at least the storage position;

a third access panel proximate the third access opening for covering the third access opening when the protection body is in at least the storage position;

a fourth access panel proximate the fourth access opening for covering the fourth access opening when the protection body is in at least the storage position;

a lateral crease forming a flap proximate a distal end;

a plurality of fasteners coupled to the flap for closing the flap around a portion of the patient when in the deployed position;

wherein the medical device in plan view in the storage position has a first narrowing portion and a second narrowing portion resembling in shape an hourglass; and wherein the at least one fastener comprises a hook-and-loop closure.

* * * * *